United States Patent
Anderson et al.

(10) Patent No.: US 9,936,973 B2
(45) Date of Patent: *Apr. 10, 2018

(54) SEALED DISTAL END PROSTHESIS INSERTION BAG

(71) Applicant: Robert G. Anderson, Aledo, TX (US)

(72) Inventors: Robert G. Anderson, Aledo, TX (US); Jon Cameron, Dallas, TX (US)

(73) Assignee: Robert G. Anderson, Aledo, TX (US)

( * ) Notice: Subject to any disclaimer, the term of this patent is extended or adjusted under 35 U.S.C. 154(b) by 42 days.

This patent is subject to a terminal disclaimer.

(21) Appl. No.: 15/261,196

(22) Filed: Sep. 9, 2016

(65) Prior Publication Data
US 2016/0374720 A1    Dec. 29, 2016

Related U.S. Application Data

(60) Provisional application No. 62/348,338, filed on Jun. 10, 2016.

(51) Int. Cl.
| | |
|---|---|
| *A61F 2/12* | (2006.01) |
| *A61B 17/34* | (2006.01) |
| *A61F 2/00* | (2006.01) |
| *A61B 17/02* | (2006.01) |
| *A61B 17/00* | (2006.01) |

(52) U.S. Cl.
CPC ........ *A61B 17/3468* (2013.01); *A61F 2/0095* (2013.01); *A61B 17/02* (2013.01); *A61B 2017/00796* (2013.01); *A61F 2/12* (2013.01); *A61F 2230/0067* (2013.01)

(58) Field of Classification Search
CPC ....................................................... A61F 2/12

USPC .......................................................... 623/7–8
See application file for complete search history.

(56) References Cited

U.S. PATENT DOCUMENTS

| | | | |
|---|---|---|---|
| 4,641,648 | A | 2/1987 | Shapiro |
| 4,995,906 | A | 2/1991 | Iwasaki et al. |
| 5,571,178 | A | 11/1996 | Ledergerber |
| 5,723,006 | A | 3/1998 | Ledergerber |
| 5,782,913 | A | 7/1998 | Schindler et al. |
| 8,206,443 | B2 | 6/2012 | Preissman |
| 8,211,173 | B2 | 7/2012 | Keller et al. |

(Continued)

FOREIGN PATENT DOCUMENTS

WO    WO/2013/122568 A1    8/2013

OTHER PUBLICATIONS

Richard A. Mladick, M.D., F.A.C.S. "No-Touch" Submuscular Saline Breast Augmentation Technique, Aesthetic Plastic Surgery, 17:183-192, 1993, New York, NY.

(Continued)

*Primary Examiner* — Suzette J Gherbi
(74) *Attorney, Agent, or Firm* — Kirby B. Drake; Klemchuk LLP (57) ABSTRACT

An apparatus and method for inserting prosthesis implants into a patient pocket. The apparatus has two openings including a prosthesis opening and a proximal opening. The prosthesis bag is a container with a wide sealed distal end and passage to a narrow apex. The apparatus reduces infection; eases insertion and placement of a cohesive silicone gel implant; and reduces complications. In use, the prosthesis bag is placed through the patient incision while allowing the bag to be manipulated to force the prosthesis into a surgical pocket of a patient.

5 Claims, 13 Drawing Sheets

(56) References Cited

U.S. PATENT DOCUMENTS

| | | |
|---|---|---|
| 8,313,760 B2 | 11/2012 | Hunter |
| 8,550,090 B2 | 10/2013 | Keller et al. |
| 8,555,893 B2 | 10/2013 | Keller et al. |
| 8,641,758 B1 | 2/2014 | Anderson |
| D736,372 S | 8/2015 | Anderson |
| D738,490 S | 9/2015 | Anderson |
| D742,509 S | 11/2015 | Anderson |
| D752,739 S | 3/2016 | Anderson |
| 9,474,593 B2 * | 10/2016 | Anderson ............... A61F 2/12 |
| 9,782,251 B2 * | 10/2017 | Anderson ............... A61F 2/12 |
| 9,808,285 B2 * | 11/2017 | Anderson .......... A61B 17/3468 |
| 2007/0276484 A1 | 11/2007 | Abell et al. |
| 2009/0204107 A1 | 8/2009 | Keller et al. |
| 2010/0280610 A1 * | 11/2010 | Preissman ............... A61F 2/12 |
| | | 623/8 |
| 2011/0035003 A1 | 2/2011 | Preissman |
| 2011/0082546 A1 * | 4/2011 | Freund ................... A61F 2/12 |
| | | 623/8 |
| 2011/0218624 A1 | 9/2011 | Preissman |
| 2012/0185042 A1 | 7/2012 | Preissman |
| 2012/0259414 A1 | 10/2012 | Preissman |
| 2013/0073040 A1 | 3/2013 | Preissman |
| 2014/0074235 A1 | 3/2014 | Keller et al. |
| 2014/0074236 A1 | 3/2014 | Keller et al. |
| 2014/0148901 A1 | 5/2014 | Anderson |
| 2014/0228951 A1 * | 8/2014 | Zochowski ............ A61F 2/12 |
| | | 623/8 |
| 2015/0126812 A1 | 5/2015 | Anderson |
| 2015/0374478 A1 | 12/2015 | Anderson |
| 2016/0038275 A1 * | 2/2016 | Preissman ............... A61F 2/12 |
| | | 623/8 |
| 2016/0095697 A1 * | 4/2016 | Anderson ............... A61F 2/12 |
| | | 623/8 |
| 2017/0014158 A1 * | 1/2017 | Anderson ............. A61B 17/02 |
| 2017/0100233 A1 * | 4/2017 | Zochowski ............. A61F 2/12 |
| 2017/0354488 A1 * | 12/2017 | Anderson ............ A61F 2/0095 |

OTHER PUBLICATIONS

Richard A. Mladick, M.D., F.A.C.S. Significance of *Staphylococcus epidermidis* Causing Subclinical Infection, Plastic & Reconstructive Surgery: Apr. 15, 2005—vol. 115—Issue 5—pp. 1426-1427, Virginia Beach, VA.

Richard A. Mladick, M.D., F.A.C.S. Prevention of Capsular Contracture, Plastic & Reconstructive Surgery: May 1999—vol. 103—Issue 6—pp. 1773-1774, Virginia Beach, VA.

Thomas M. Biggs, M.D. Prefilled Saline Breast Implants Offer Significant Advantages, Aesthetic Surgery Journal Sep. 1999 vol. 19 No. 5 424, St Louis, MO.

"Mitchel H. Brown, M.D.., M.Ed. Cohesive Silicone Gel Breast Implants in Aesthetic and Reconstructive Breast Surgery, Plastic & Reconstructive Surgery: Sep. 1, 2005—vol. 116—Issue 3—pp. 768-779".

* cited by examiner

SEALED DISTAL END PROSTHESIS INSERTION BAG

BACKGROUND

Field of Invention

These inventions relate to the apparatus and method of safely inserting a prosthesis into a human body.

Background of the Invention

The present inventions are useful and novel apparatuses for advancing breast implant surgery procedures to improve surgical sterility.

Breast implants are a manufactured prosthesis used in cosmetic and reconstructive surgery. A breast implant has an outer casing or membrane that is filled with a fluid such as saline or a gelatinous cohesive silicone.

Only about thirty percent (30%) of breast implant procedures today use an insertion device. An insertion device shortens the duration of the surgical procedure and improves the patient outcome. In regard to a cohesive silicone gel implant, without an insertion device, the surgeon makes the incision, creates a pocket for the implant, retracts the incision and then manually pushes the implant across the skin through the incision into the pocket.

Different than a silicone gel filled implant, a saline implant is inserted into the pocket in an empty configuration. Once placed in the pocket, the surgeon takes the additional step of filling the implant with a saline solution using a tube.

The incision is made in one of four places: in the armpit, in the breast fold, in the navel, or around the areola. Except for the navel insertion, one incision is made for each implant. It is preferable that the incision be as short as possible. Shorter incisions are less unsightly. This goal of a shorter incision is easier to accomplish with a saline implant. A saline implant is relatively easy to insert through a short incision, as the bladder is unfilled and therefore small in size as it passes through the incision. For these inflatable implants, the surgeon rolls up the implant like a cigar and pushes it through the incision and into the pocket. In contrast, silicone implants are prefilled resulting in a more difficult and complications-susceptible operation. For these pre-filled implants, the procedure requires a longer incision length.

After the initial incisions, the surgeon dissects a path through the tissue to the desired destination of the implant. Once that path has been created, a pocket is created for the implant superficial or deep to the pectoralis major muscle. The pocket may be formed in one of two places under the breast: subglandular (between the breast tissue and pectoralis major muscle) or subpectoral (under the pectoralis major muscle). Subglandular places the prosthesis directly behind the mammary gland and in front of the muscle. Subpectoral places the implant partially under the pectoralis major muscle. Due to the shape of the pectoralis major muscle, a portion of the implant is not covered by the muscle.

A secondary surgery is common for patients with breast implants. In particular, patients with breast implants may require surgery to change the placement (from subglandular to subpectoral or vice versa), correct palpable folding of the implant, remove a ruptured implant; treat infection, bleeding, breast pain, contracted scar tissue forming around the implant (capsular contracture) and collections of fluid around the implant. These additional surgeries have risks due to anesthesia, infection and bleeding. The overall secondary operation complication rate is almost 20% for silicone gel breast augmentation within 3 years of the initial operation and up to 36-45% by 10 years from the initial breast implant surgery. The majority of re-operations are related to implant rupture (leakage), bleeding or capsular contracture.

Cellulitis, a skin-based infection, occurs in 2%-4% of patients, with some surgeons reporting much higher rates, and is usually from the bacteria normally present on the skin. Symptoms of infection include fever, pain, swelling and redness. To reduce infection, surgeons give a single dose of antibiotics before the surgery, and use an antibiotic solution in the wound before implant placement. The antibiotic solution may double as the lubrication to allow easier insertion of the implant into the pocket. However, surgeons can bring the rate of capsular contracture and infection down further by preventing the implant from touching the patient's skin.

The implant insertion devices heretofore known suffer from a number of disadvantages:

1. Distal end of the device is unsealed which allows the implant to inadvertently slip out of the device resulting in skin bacteria transferring to the implant.
2. The high cost of current implant devices encourages re-use despite the manufacturer recommendation not to do so.

SUMMARY OF THE INVENTION

An invention, which meets the needs stated above, is a system and method to insert a prosthesis into a patient. The prosthesis bag is a container with a wide sealed distal end and passage to a narrow apex.

The device maintains the implant in the interior and only allows exit through the proximal end.

Objects and Advantages

Accordingly, besides the objects and advantages of the system for a breast implant insertion device described above, several objects and advantages of the present invention are:
  a) to provide a device that only permits the implant to exit through the proximal end;
  b) to provide a simplified insertion method;
  c) to provide the means to reduce anesthesia time;
  d) to provide a single device that fits all sizes of implants;
  e) to provide an easier manipulation of the implant.

Further objects and advantages of this invention will become apparent from a consideration of the drawings and the ensuing description of the drawings.

DRAWING FIGURES

The accompanying drawings, which are incorporated in and constitute a part of this specification, illustrate embodiments of the present invention and together with the description, serve to explain the principles of this invention. In the figures.

KEY TERMS distal: the most distant portion from the point of attachment to the body inferior: closer to the feet lateral: a position substantially located in any side of the longitudinal position of a patient's supine position longitudinal: a lengthwise, or the longest, direction related to the patient's supine position proximal: the closest portion from the point of attachment to the body superior: closer to the head of the body

REFERENCE NUMERALS IN DRAWINGS

10 patient
20 patient's incision, opening
22 patient's breast
24 patient's implant pocket
28 patient's skin tissue
30 prosthesis
32 breast implant, implant
40 prosthesis bag, bag
42 proximal end, proximal opening
44 sealed distal end, distal end
46 base fold
48 initial fold
50 exterior tab
52 internal tab
54 prosthesis opening
56 seal folds
57 tab-side seal tuck
58 distal end seal tuck
60 lubricant
70 retractor
72 retractor handle
74 retractor handle proximal end
76 retractor proximal end lip
80 distal pouch

DETAILED DESCRIPTION OF THE DRAWINGS

Referring to the drawings, in which like numerals represent like elements,

FIGS. 1-7

Figure 1:
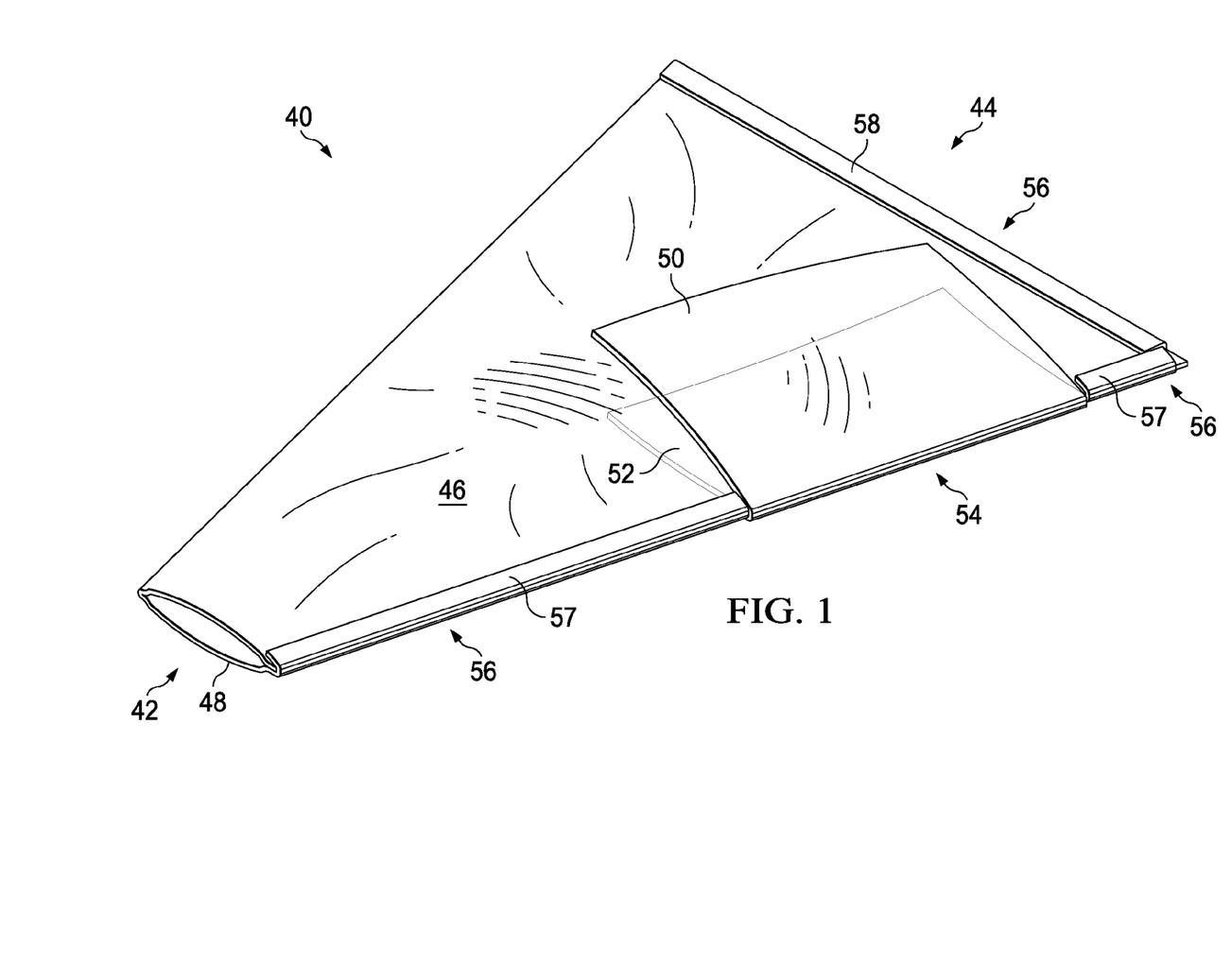
FIG. 1: Top side perspective view of a prosthesis bag.

Referring now to FIG. 1, the top side perspective view of a prosthesis bag 40 manufactured with a sheet material such as plastic or a flexible, surgical-grade nylon. The plastic may be strengthened or reinforced with fibers. The prosthesis bag 40 may be clear, or semi-transparent, to allow observation of the prosthesis 30 moving from the bag 40 into the patient pocket 24.

The prosthesis bag 40 has two openings: a proximal opening 42 for inserting into the incision 20 and a prosthesis opening 54, surrounded by an exterior tab 50 and an internal tab 52, for inserting the prosthesis 30 into the prosthesis bag 40. FIG. 1 shows the tabs 50,52 located proximally to the sealed distal end 44 and the internal tab 52 pushed through the prosthesis opening 54, to prevent the implant from passing to the outside of the insertion device 40, and the exterior tab 50 folded over the prosthesis opening 54. The exterior tab 50 may be folded and held in place by friction or attached by glue, adhesive, heat bond, surgical tape or other coupling mechanism. While FIG. 1 shows both tabs 50,52 folded into the working position, the exterior tab 50 and internal tab 52 would initially be presented to the surgeon with both tabs 50, 52 outside of the prosthesis bag 40 and surrounding the prosthesis opening 54. While the preferred embodiment shows different sized tabs 50,52 to distinguish the exterior tab 50 from the internal tab 52, the tabs 50, 52 may be of the same size.

The prosthesis bag 40 is assembled using the seal tucks 56 which comprise two (2) tab-side seal tucks 57, and one (1) distal end seal tuck 58. In a preferred embodiment, the assembly may be done prior to packaging and shipping to the surgeon. In an alternate embodiment, the seal tucks 56 are sealed to the base fold 46 by the patient's 10 operating team. See FIG. 9B for additional illustration of the assembly using the seal tucks 56.

The prosthesis bag 40 prevents the breast implant 32 from touching the patient's skin tissue 28, prevents the implant 32 from inadvertently exiting the chamber, and prevents damage to the implant 32 during the implant 32 insertion. The prosthesis bag 40 may be manufactured to accommodate any breast implant 32 shape, volume, and diameter. The manufacturer may suggest specific skin incision 20 lengths to allow insertion of the implant 32 through the bag 40 into the incision 20. The specifications take the burden off the surgeon to try to make shorter incisions 20.

Figure 2:
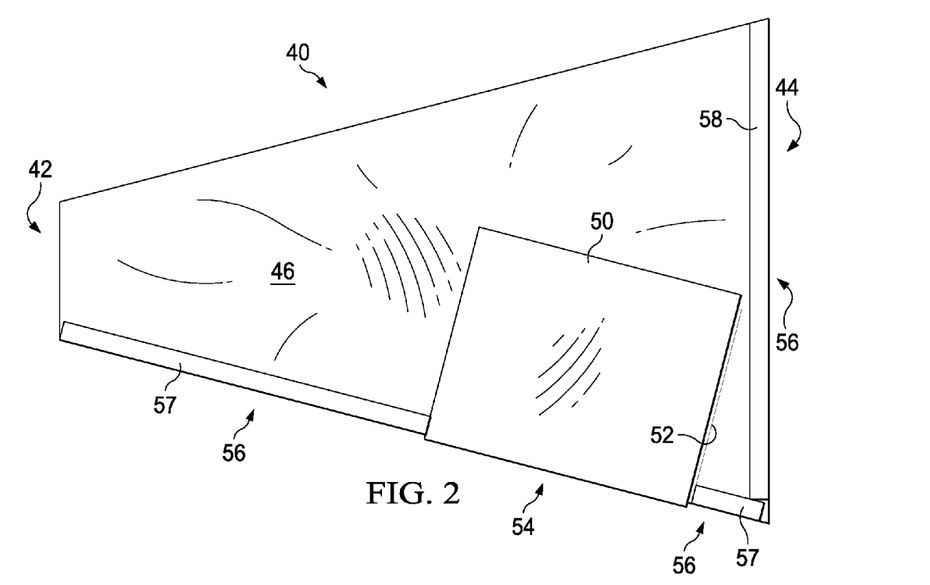
FIG. 2: Top view of a prosthesis bag.
Figure 3:
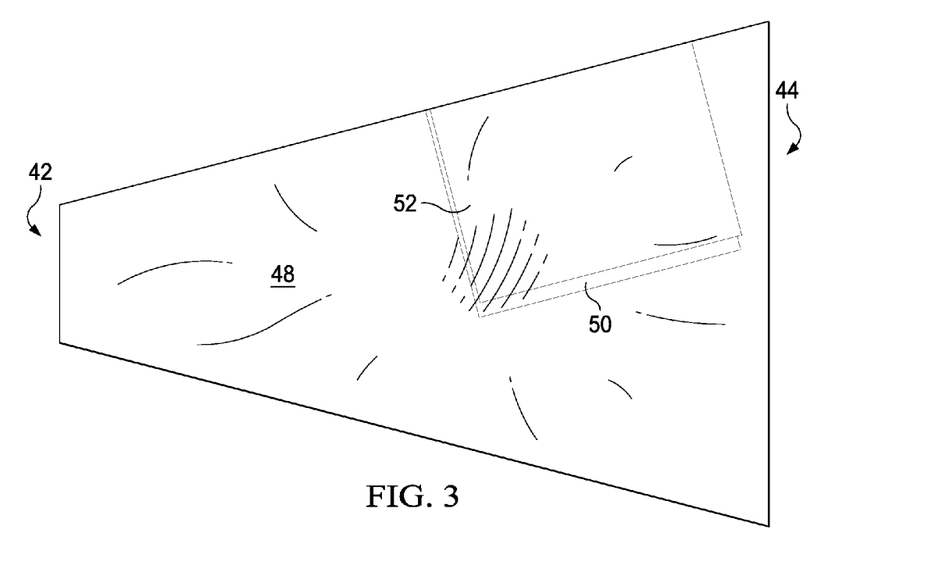
FIG. 3: Bottom view of a prosthesis bag.

FIGS. 2-3 shows a top and bottom view, respectively, of the manufactured version of the prosthesis bag 40 once the initial fold 48 is folded over the base fold 46 along the abutted seam and the three (3) seal tucks 56 are adhered to the base fold 46. The manufactured bag 40 comprises the initial fold 48 partially sealed on the periphery to the base fold 46, a proximal opening 42, a sealed distal end 44, a prosthesis opening 54, an exterior tab 50 and an internal tab 52. The seal folds 56 comprise tab side seal tucks 57 and a distal end seal tuck 58. The internal tab 52 is folded through the prosthesis opening 54 and the exterior tab 50 is then folded over the prosthesis opening 54 to secure the opening 54 and prevent the inadvertent exit of the implant 32.

Figure 4:
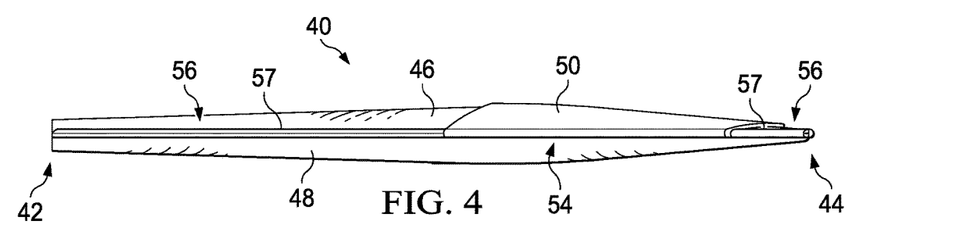
FIG. 4: Right view of a prosthesis bag.
Figure 5:
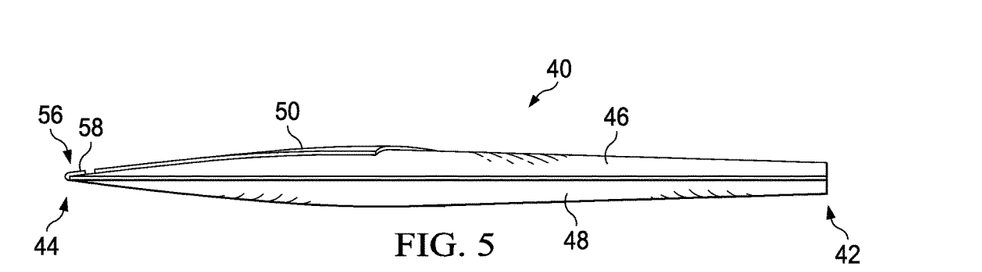
FIG. 5: Left view of a prosthesis bag.
Figure 6:
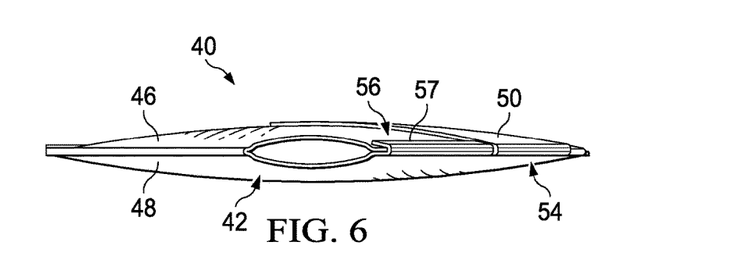
FIG. 6: Proximal end view of a prosthesis bag.
Figure 7:
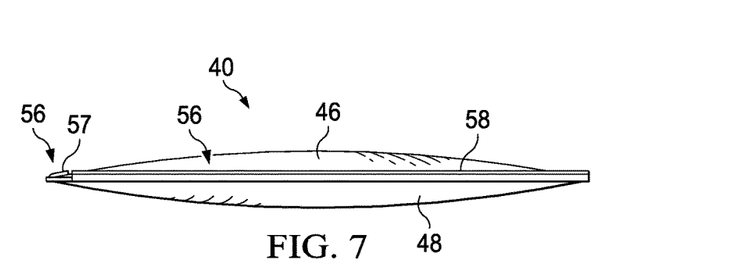
FIG. 7: Distal end view of a prosthesis bag.

FIG. 4 shows the right side of the prosthesis bag 40 with the exterior tab 50 folded over the base fold 46. FIG. 5 illustrates the prosthesis bag 40 with the proximal opening 42 located parallel to the distal end seal tuck 58. FIG. 6 shows the proximal end 42 with the proximal opening 42. FIG. 7 illustrates the distal end 44 with the distal end seal tuck 58.

Figure 8:
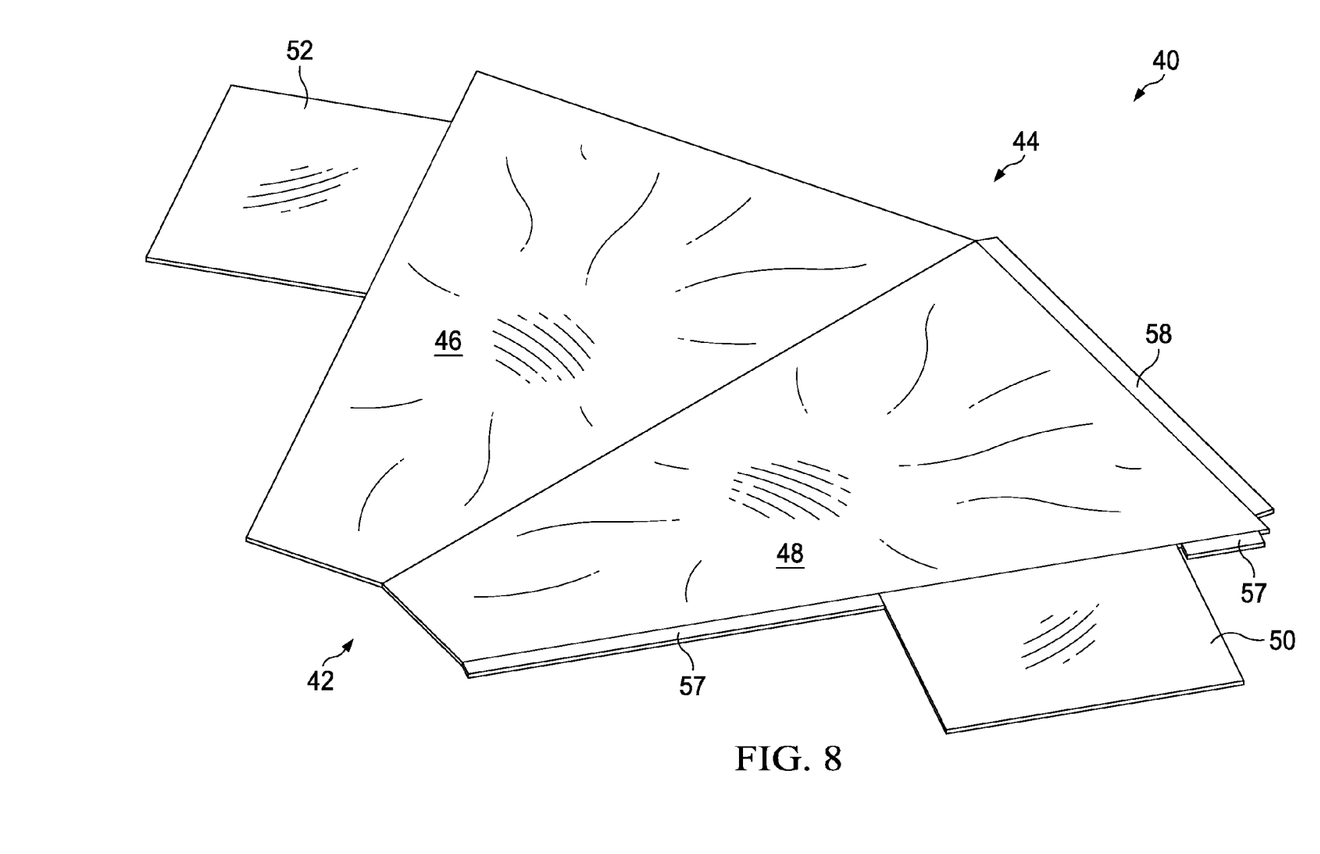
FIG. 8: Top side perspective view of an unassembled a prosthesis bag attached to the initial fold.
Figure 9A:
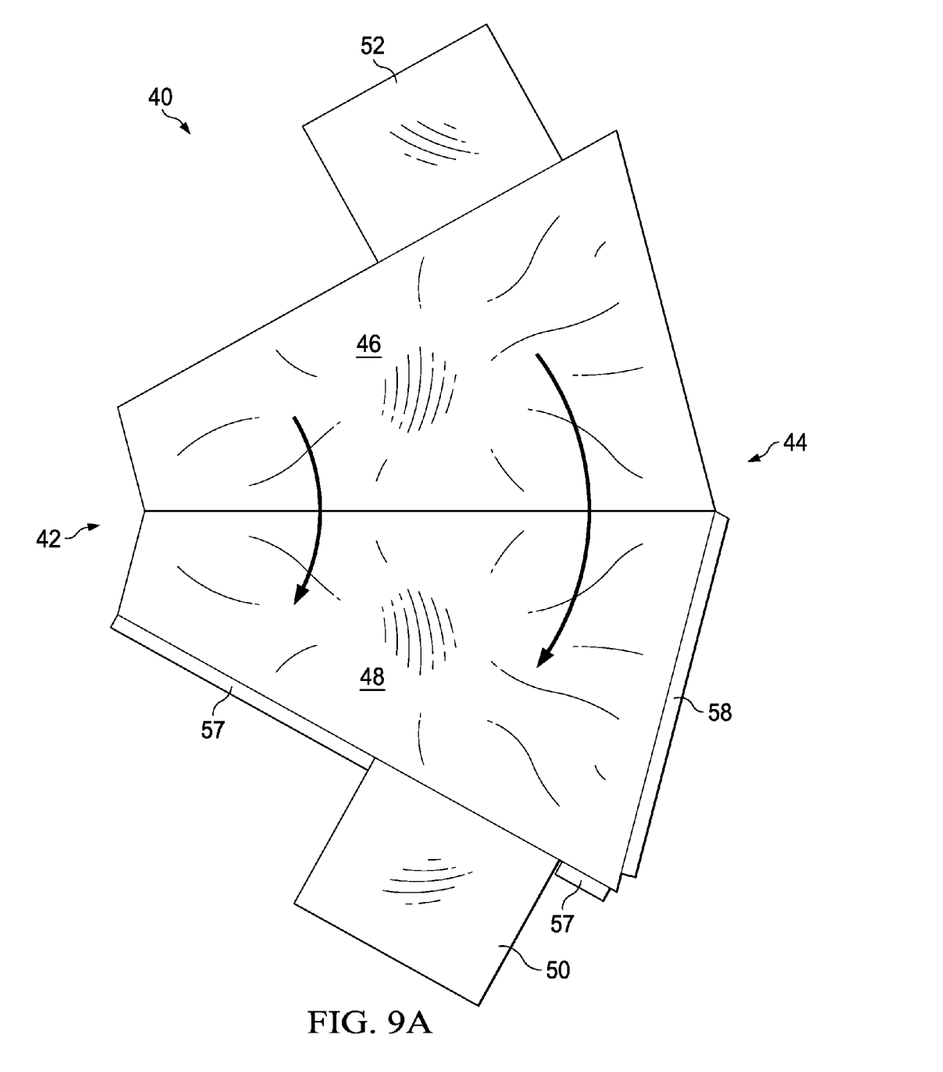
FIG. 9A: Top view of a prosthesis bag being folded along the abutted edges.
Figure 9B:
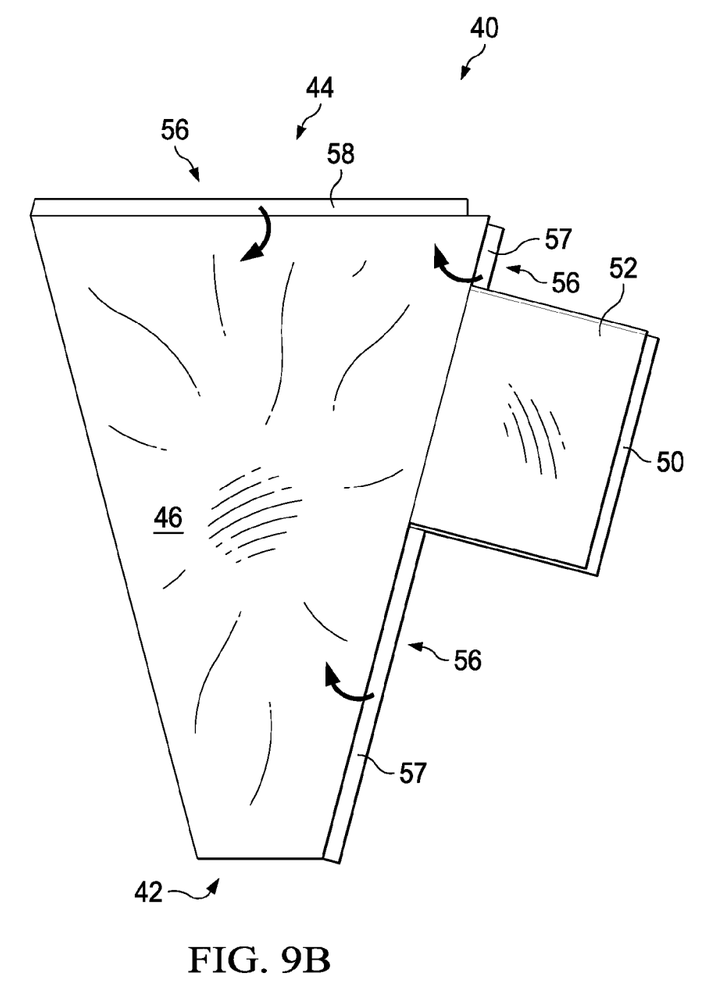
FIG. 9B: Top view of a prosthesis bag showing the base fold assembled over the initial fold.
Figure 9C:
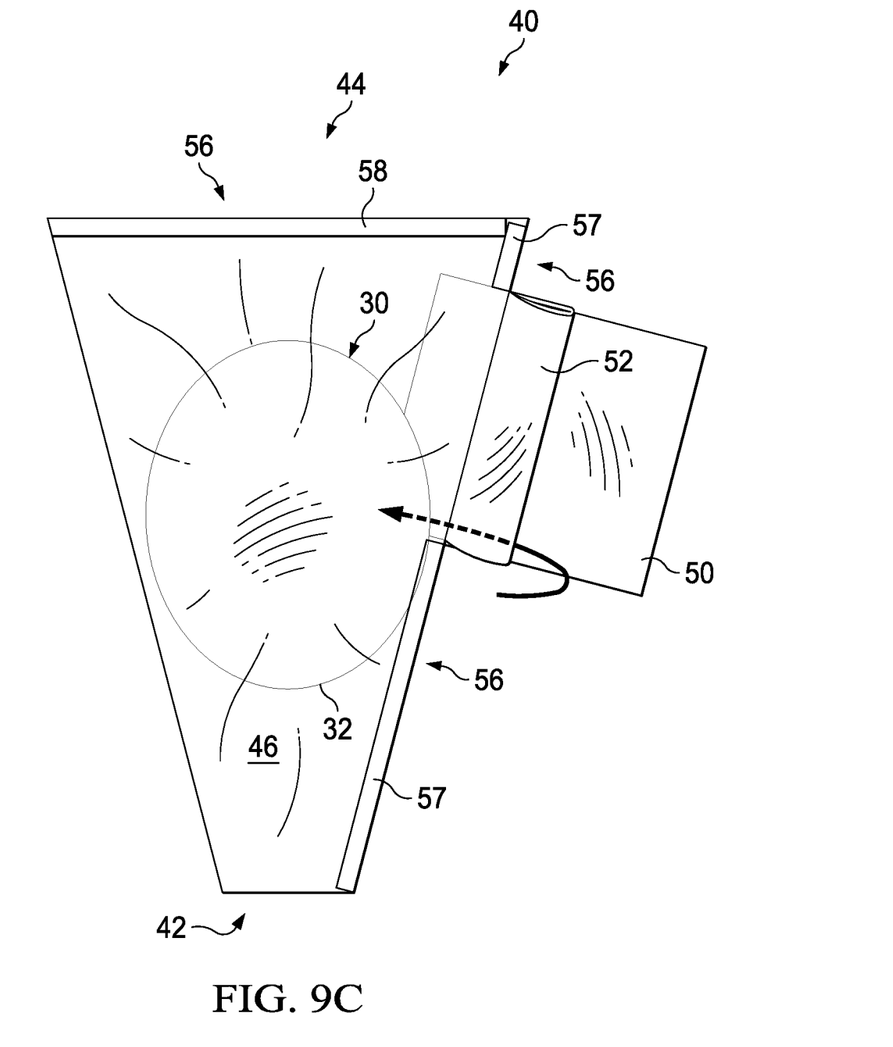
FIG. 9C: Top view of a prosthesis bag with the internal tab folded through prosthesis opening after the prostheses are inserted.
Figure 9D:
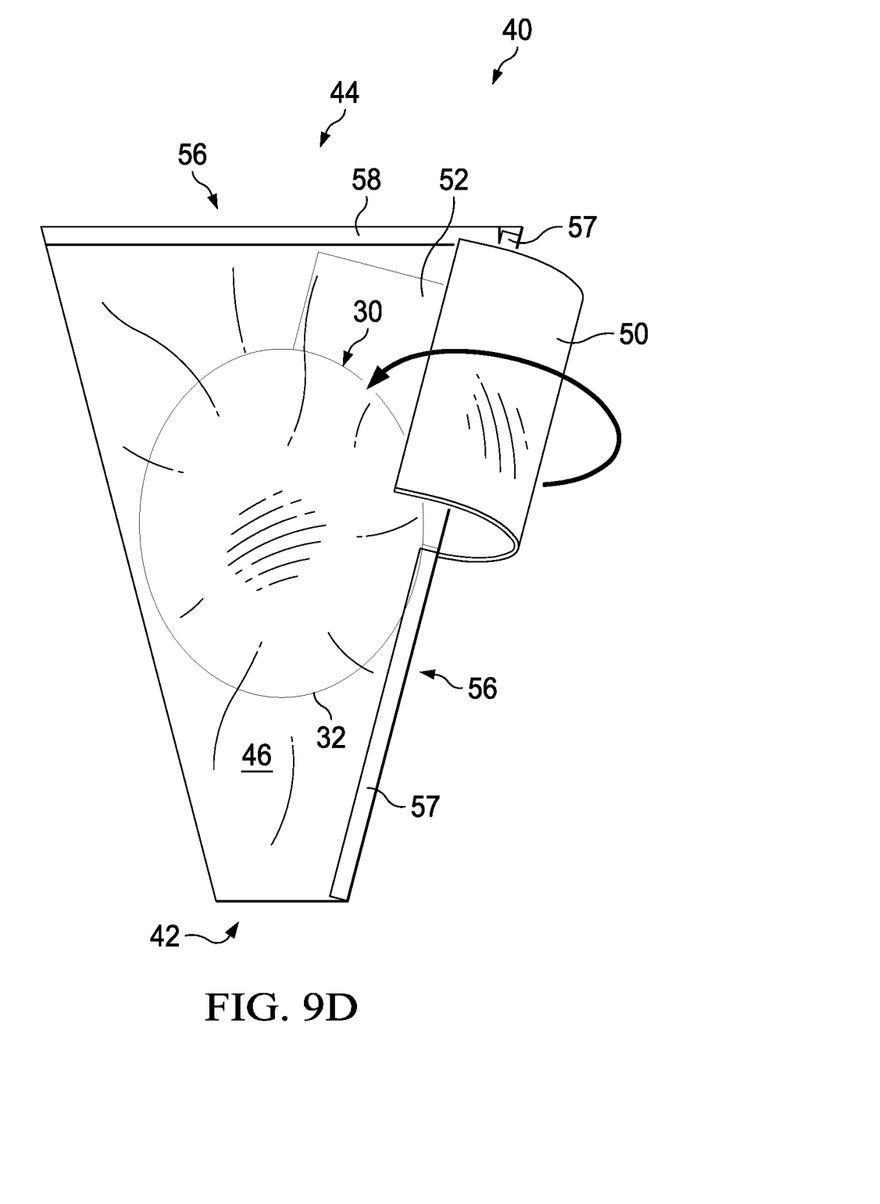
FIG. 9D: Top view of a prosthesis bag with the exterior tab being folded over the prosthesis opening.

FIGS. 8-9D

Turning to FIG. 8, the illustration depicting a perspective view of an unassembled prosthesis bag 40. The prosthesis bag 40 form comprises two folds 46, 48 with opposing prosthesis insertion tabs 50, 52. In a preferred embodiment the tabs 50,52 are located distally and opposing the abutted sides of the manufactured prosthesis bag 40. In a preferred embodiment, as shown in FIGS. 3-4D, the base fold 46 is manufactured abutted against the initial fold 48 along either edge opposing the tabbed side of the folds 46,48. In a second embodiment the initial fold 48 and base fold 46 would be separately manufactured and assembled together at a later stage.

In the preferred embodiment, the prosthesis bag 40 would be folded along an abutted edge and manufactured with three seal tucks 56 along:
 a. initial fold's 48 sealed distal end 44 from the abutted side to the tab side;
 b. initial fold's 48 tab-side edge from the exterior tab 50 to the proximal end 42;
 c. initial fold's 48 tab-side edge from the exterior tab 50 to the sealed distal end 44.

In another embodiment, the seal tucks 56 may be replaced with a simple seam along the edges to bind the initial fold 48 and based fold 46 with glue, adhesive, heat bond, surgical tape or other coupling mechanism.

FIGS. 9A to 9D show the assembly of the prosthesis bag 40. In FIG. 9A, the pattern is folded along the abutted edge so that base fold 48 and initial fold 46 are stacked over each other with the tabs 50, 52 pointing to the side and in the same direction.

Then in FIG. 9B, the seal tucks 56 are folded over the opposing fold 46, 48 and sealed to the opposing fold 46, 48 with any desired manufacturing sealing technique. The tabs remain unfolded until the breast implant 32 and lubricant 60 are placed inside the bag 40.

With the breast implant 32 in place inside the prosthesis bag 40, in FIG. 9C, the internal tab 52 is pushed through the prosthesis opening 54. The internal tab 52 prevents the implant 32 from inadvertently ejecting through the prosthesis opening 54 during the operation.

In FIG. 9D, with the internal tab 52 inside the prosthesis opening 54, the exterior tab 50 may be pushed over the top surface of the opposing fold 46, 48. The exterior tab 50 may be sealed to the opposing fold 46, 48 with surgical tape, heat seal, instant glue, or other forms of seals. The adhered seal 50 opposes the prosthesis opening 54 and joins the initial fold 48 and base fold 46.

Figure 10:
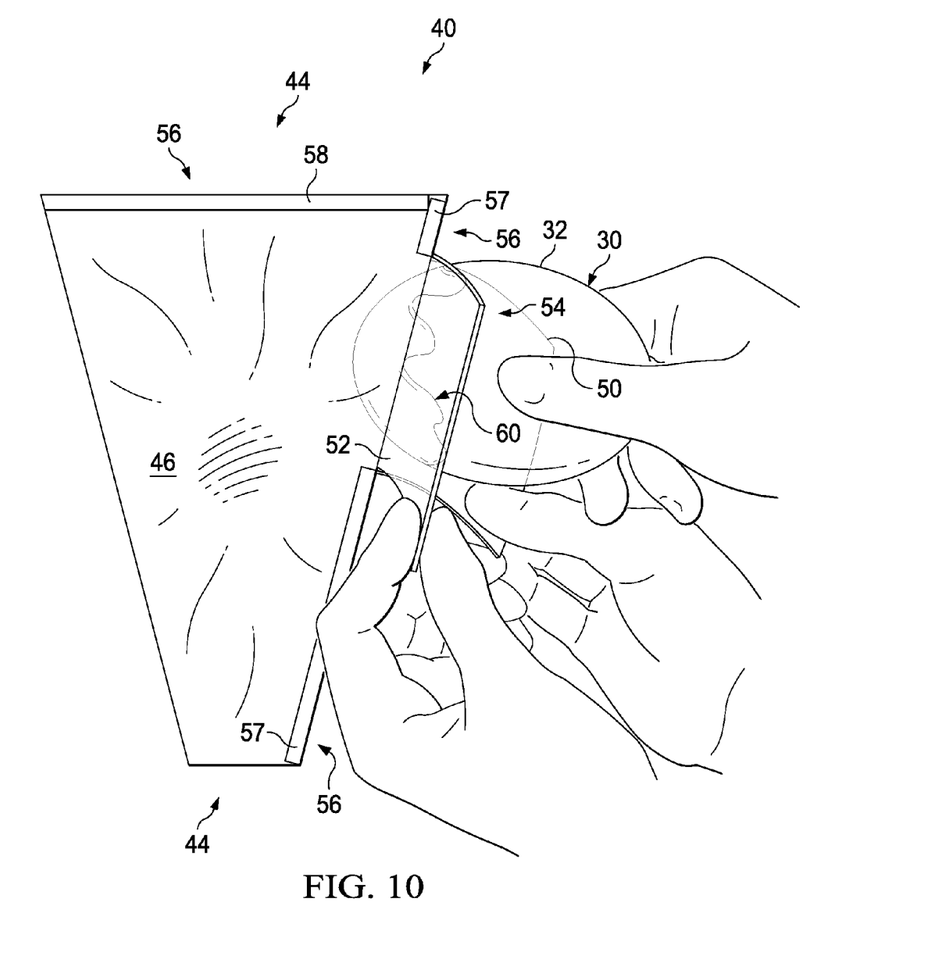
FIG. 10: Front perspective view of a prosthesis bag with an implant being inserted through the prosthesis opening.
Figure 11:
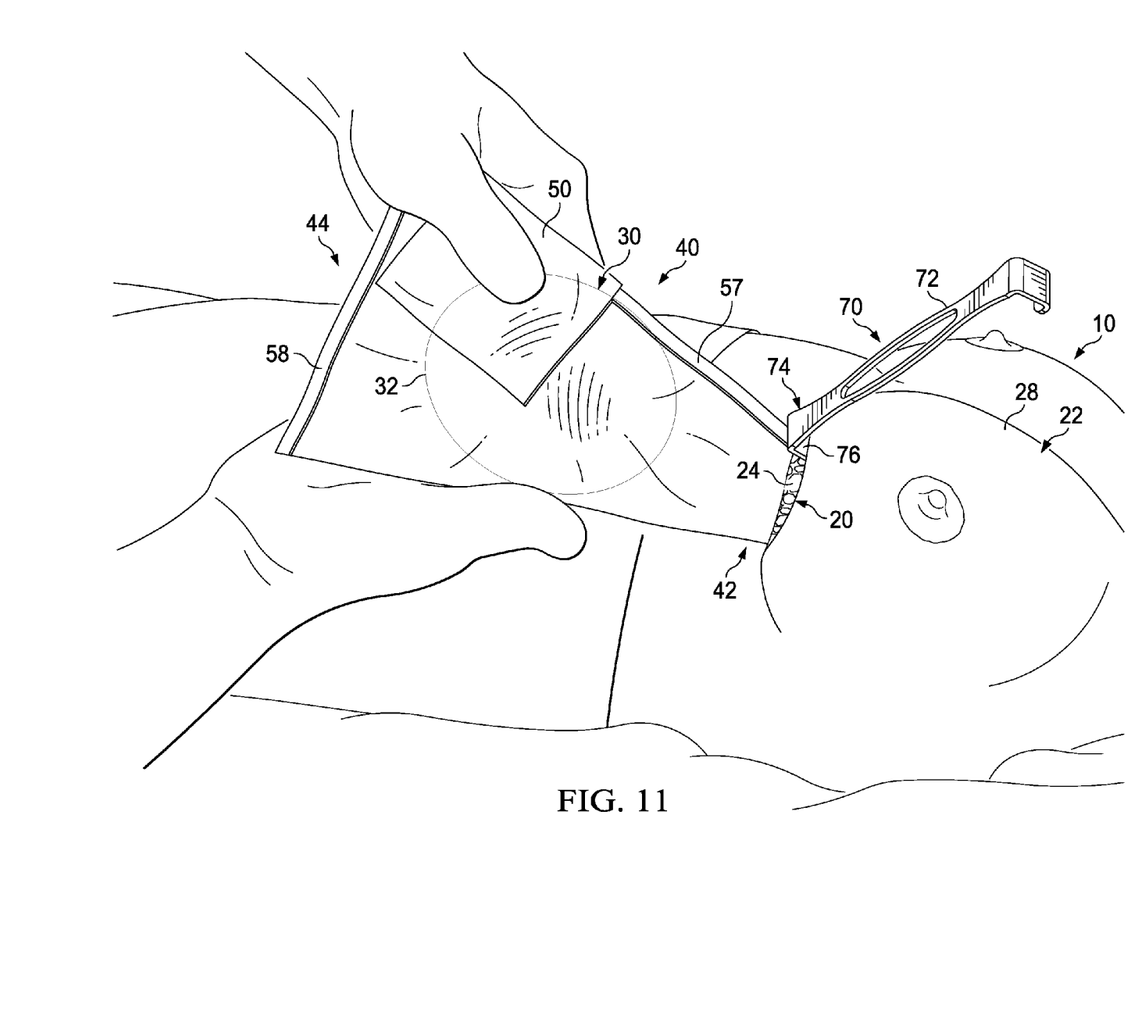
FIG. 11: Left side perspective view of a prosthesis bag with the proximal end inserted into the left patient incision.

FIGS. 10-11

As illustrated in FIG. 10, in the preferred embodiment a liquid lubricant 60 surrounds the breast implant 32 inside the prosthesis bag 40. A coating of surgical lubricant 60 may be used on the inner surface of the prosthesis bag 40. As an alternative, the insertion device 40 may be provided with a coating that becomes slick when wet. In still another alternative, the prosthesis 30 may be provided with a slick surface, such as a surgical lubricant 60. The surgeon also has the option of applying a lubricant 60 to the prosthesis 30 directly before inserting into the prosthesis bag 40. The lubricant 60 may also act as an antibiotic solution.

After lubrication, the breast implant 32 is inserted into the device 40 by the surgeon and nurse. To do so, the nurse opens the prosthesis opening 54 by separating the tabs 50, 52, and the surgeon slides the prosthesis 30 through the prosthesis opening 54. The team would then fold the internal tab 52 into the prosthesis opening 54 to prevent the breast implant 32 from moving back out of the opening 54. The exterior tab 50 may be left extended or folded over the opposing fold 46, 48. If desired, the exterior tab 50 may be sealed to the opposing fold 46, 48. In a preferred embodiment inserting the prosthesis 30 into the prosthesis bag 40 would be completed prior to inserting the retractor 70 into the patient incision 20. However, a surgeon could perform this step while the bag 40 is inserted in the incision 20. In a preferred embodiment the surgeon would insert one prosthesis 30 into the prosthesis bag 40 at a time. However, a surgeon may insert both breast implants 32 before beginning the procedure.

The surgical team may insert lubricant 60 in the prosthesis opening 54. The liquid lubricant 60 surrounds the breast implant 32 inside the prosthesis bag 40. An antibiotic solution may be used as lubricant 60. The tabs 50,52 may be displaced from the seal folds 56 to allow for the addition of lubricant 60 after the tabs 50,52 are folded in operational positions. If the surgeon does not want to displace the tabs 50,52 to insert lubricant, the bag 40 can be placed in a vertical position with the distal end seal tuck 58 in the lower position and insert lubricant in the proximal opening 42. The tabs 50,52 may also be designed shorter than the width of the prosthesis opening 54 so that remains a space to insert a lubrication bulb.

FIG. 11 shows the patient 10 positioned in a supine position prior to an incision 20 being made in the patient's skin tissue 28. In the figure, the incision 20 is cut in the right-side inferior breast 22 crease. With the incision 20 opened, the surgeon then forms a pocket 24 in one of two places under the breast 22: subglandular (between the breast 22 tissue and pectoralis muscle) or subpectoral (under the pectoralis muscle). The pocket 24 is sized to match the prosthesis 30 diameter. By manipulating the retractor handle 72, the retractor handle proximal end 74 and the retractor proximal lip 76 are inserted into the incision 20 to both retract the incision 20 and hold the incision 20 open.

The retractor 70 assembly comprises a handle 72 located in the center, retractor handle proximal end 74, and retractor handle proximal end lip 76. The retractor 70 may have various shapes and sizes to match the particular application or surgeon preferences. The handle 72 of the retractor 70 is bent or angled on the ends relative to the intermediate portion. The proximal end 74 of the retractor 70 has a lip 76 that is angled relative to the end 74. The retractor 70 is made of metal, such as stainless steel but may also be manufactured in a surgical plastic.

The retractor proximal end 74 is structured and arranged to be inserted through the incision 20 into a pocket 24 of a patient 10. The proximal end lip 76 helps maintain the proximal end 74 of the retractor 70 beneath skin tissue 28 of a patient 10.

The retractor 70 extends anteriorly from the prosthesis bag 40, so as not to interfere with the surgeon manipulating the bag 40, with the proximal ends of the retractor 74 and proximal end lip 76 inserted into the incision 20 and located under the skin tissue 28 and moved to retract the incision 20. The proximal end 42 of the prosthesis bag 40 may be lubricated with a lubricant 60 and inserted into the open incision 20.

The prosthesis bag 40, distal to the incision 20, is squeezed and/or twisted to force the prosthesis 30 toward the proximal end 42 of the prosthesis bag 40 and into the pocket 24. The prosthesis 30 deforms to fit through the proximal opening 42.

Once the prosthesis 30 is located inside the pocket 24, the retractor 70 is removed from the incision 20, followed by the bag 40. The incision 20 is then closed.

If the prosthesis bag 40 is designed for reuse, they are subjected to sterilization procedures. If the bag 40 is designed for single use, they are disposed of.

The implant 32 is subject to damage if the implant 32 is mishandled. Possible mishandling includes subjecting the implant 32 to undue stresses or pressures, such as may be caused by attempting to squeeze the implant 32 through a proximal end 42 that is too small, and folding of the external silastic shell, internal fracture of the cohesive silicone gel. A surgeon may make an incision 20 in the patient 10 that is too short for the implant 32 and thus too much force is required to squeeze the implant 32 into the pocket 24. With this prosthesis bag 40, the implant 32 is protected from damage by the provision an adequate skin incision length and of the properly sized proximal end 42. The major complication with implants 32 is capsular contracture thought to be due to sub-clinical infection. Sub-clinical infection is most likely caused by pushing the implant 32 through the skin incision 20, dragging natural skin 28 bacteria (still present after proper skin 28 preparations) into the pocket 24 surgically created for the implant 32. Use of this device 40 prevents the implant 32 from coming in contact with the skin tissue 28 during the insertion process.

Figure 12:
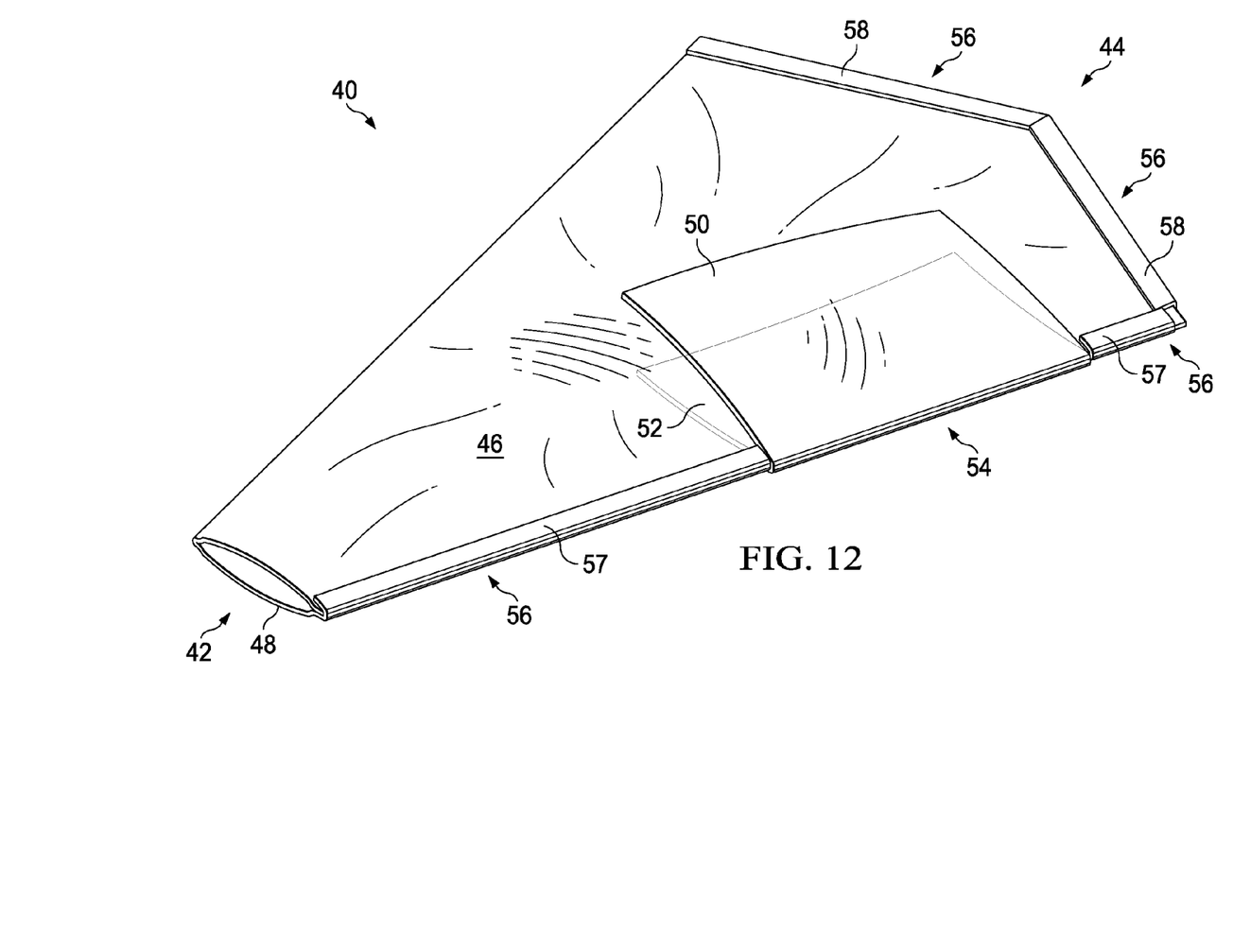
FIG. 12: Top side perspective view of a pentagon prosthesis bag showing a three-sided distal end seal tuck.
Figure 13:
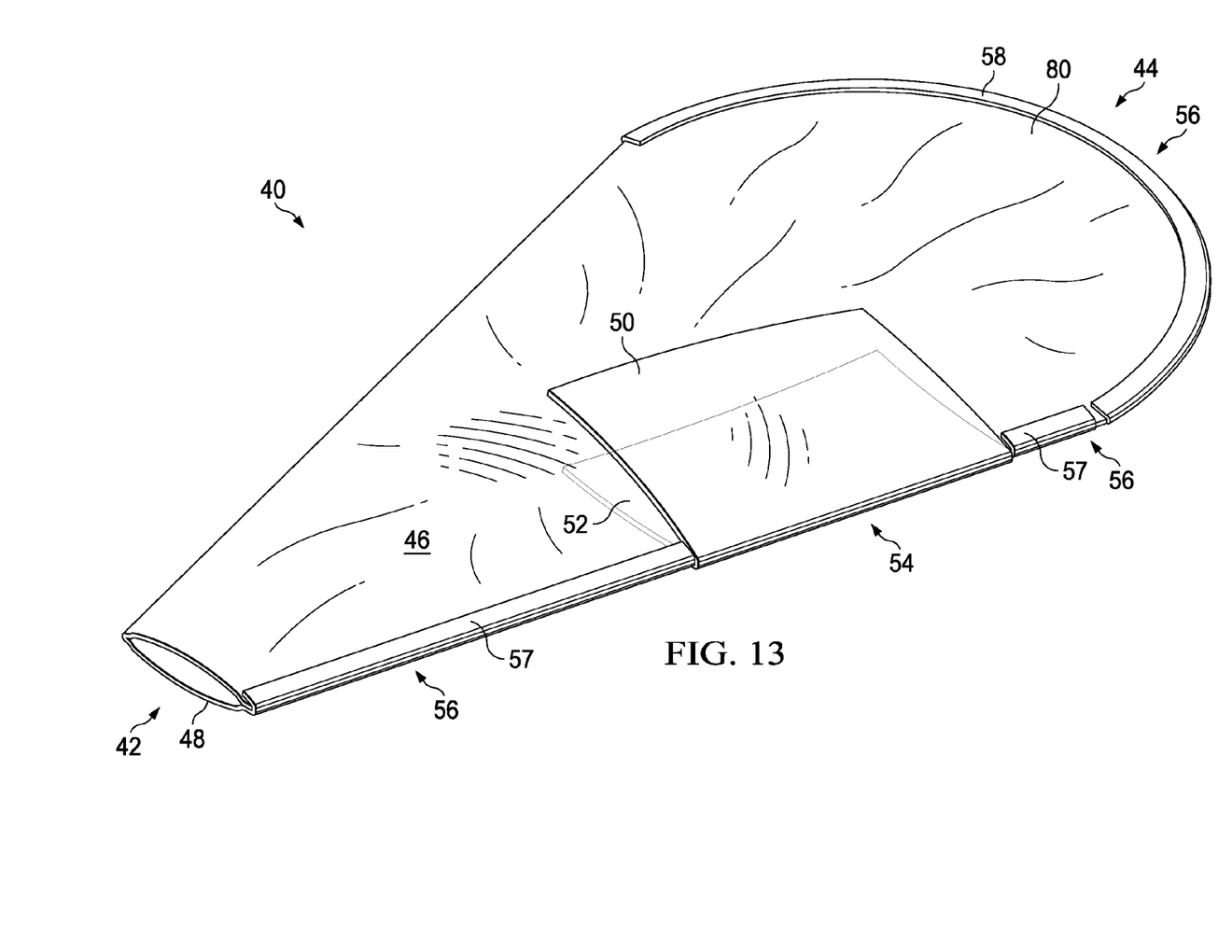
FIG. 13: Top side perspective view of a pentagon prosthesis bag showing a three-sided distal end seal tuck.
Figure 14:
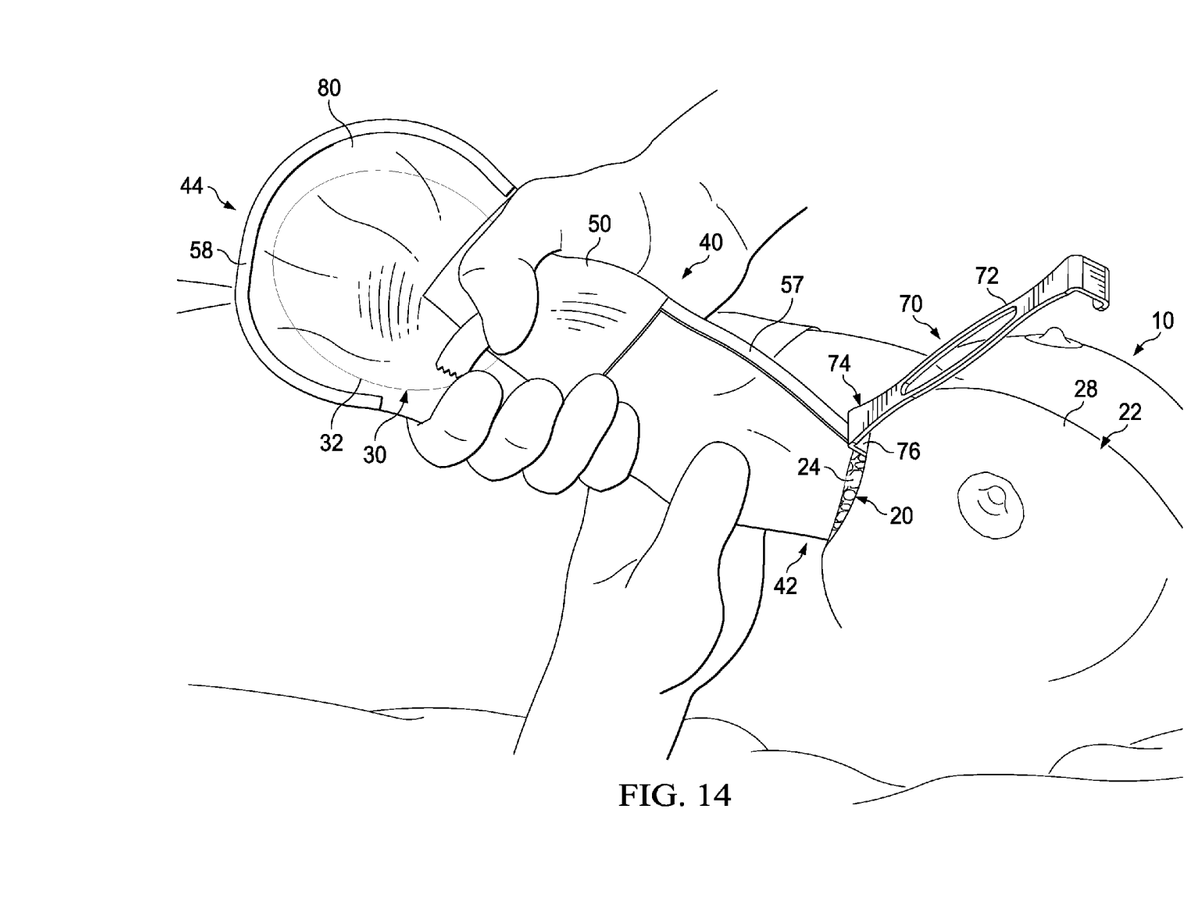
FIG. 14: Top side perspective view of a pentagon prosthesis bag with a distal pocket proximally to the distal end seal tuck.

FIGS. 12-14

The sealed distal end 44 of the prosthesis bag 40 may be of any shape desirable for efficient manufacturing and/or effective use of the bag 40. FIG. 12 demonstrates a bag 40 shaped as an irregular pentagon with two (2) angles formed in the distal end seal tuck. This improves manufacturing efficiency in a tuck folding machine versus a rounded distal end 44. The sealed distal end 58 may also be designed to improve manipulating the bag 40. In FIGS. 13-14 the sealed distal end is rounded to form a pouch 80. FIG. 13 shows a top side perspective of the rounded distal end seal tuck 58 surrounding the pouch 80. FIG. 14 demonstrates the pouch 80 in use by the surgeon where the external tab is sealed to the bag 40 with surgical tape. The surgeon may trap the prosthesis 30 in the pouch 80 by squeezing proximally to the pouch 80. With the bag 40 and prosthesis 30 stabilized in her left hand, the surgeon can then use his/her right hand to place the proximal end 42 of the bag 40 into the patient's opening 20. The surgeon then releases the prosthesis 30 from the pouch 80 and moves it toward the proximal opening 42 and into the patient's implant pocket 24. Alternately, the surgeon may trap the prosthesis 30 in the pouch 80 by using a banding or clamping tool proximal to the pouch 80. The rounded design of the distal seal tuck 58 thus provides a more effective use of the bag 40.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

In the foregoing description, and the following claims, method steps and/or actions are described in a particular order for the purposes of illustration. It should be appreciated that in alternate embodiments, the method steps and/or actions may be performed in a different order than that described. Additionally, the methods described above may be embodied in machine-executable instructions stored on one or more machine-readable mediums, such as disk drives, thumb drives or CD-ROMs. The instructions may be used to cause the machine (e.g., computer processor) programmed with the instructions to perform the method. Alternatively, the methods may be performed by a combination of hardware and software. While illustrative and presently preferred embodiments of the invention have been described in detail herein, it is to be understood that the inventive concepts may be otherwise variously embodied and employed, and that the appended claims are intended to be construed to include such variations, except as limited by the prior art.

Benefits, other advantages, and solutions to problems have been described herein with regard to specific embodiments. However, the advantages, associated benefits, specific solutions to problems, and any element(s) that may cause any benefit, advantage, or solution to occur or become more pronounced are not to be construed as critical, required, or essential features or elements of any or all the claims of the invention. As used herein, the terms "comprises", "comprising", or any other variation thereof, are intended to cover a non-exclusive inclusion, such that a process, method, article, or apparatus composed of a list of elements that may include other elements not expressly listed or inherent to such process, method, article, or apparatus.

Advantages

From the description above, a number of advantages become evident for the "Sealed Distal End Prosthesis Insertion Bag." The present invention provides all new benefits for participating parties including manufacturers, patients and surgeons:
a) allows patients a lower risk of complications;
b) allows patients to be under anesthesia for a shorter period of time;
c) allows surgeons to prevent contamination of the implant by inadvertent extrusion because of a sealed distal end;
d) allows surgeons to eliminate damage to the implant during the insertion process;
e) allows surgeons a simplified insertion process;
f) allows surgeons to perform a faster implant surgery.

The invention claimed is:

1. An apparatus for inserting a prosthesis through an incision into a surgical pocket, comprising:
 a. a breast implant;
 b. a prosthesis bag comprising a prosthesis opening, a proximal opening to allow breast implants to exit and a sealed distal end to prevent the breast implants from exiting, the prosthesis opening surrounded by tabs, the prosthesis bag being semi-rigid and structured and arranged to receive the breast implant through the prosthesis opening, the prosthesis bag assembled with tab-side seal tucks and a distal end seal tuck;

c. a retractor device, the retractor having a proximal end that is adjacent to the proximal opening and are structured and arranged to engage an edge of a surgical pocket opening, the proximal end being fixed relative to the proximal end of the prosthesis bag.

2. The apparatus of claim 1, wherein said seal distal end comprises a two-sided distal end seal tuck.

3. An apparatus for inserting a prosthesis through an incision into a surgical pocket, comprising:
   a. a breast implant;
   b. a prosthesis bag comprising a prosthesis opening, a proximal opening to allow breast implants to exit and a sealed distal end to prevent the breast implants from exiting, the seal distal end forming a distal pocket, the prosthesis opening surrounded by tabs, the prosthesis bag being semi-rigid and structured and arranged to receive the breast implant through the prosthesis opening, the prosthesis bag assembled with tab-side seal tucks and a distal end seal tuck;
   c. a retractor device, the retractor 1 having a proximal end that is adjacent to the proximal opening and are structured and arranged to engage an edge of a surgical pocket opening, the proximal end being fixed relative to the proximal end of the prosthesis bag.

4. An apparatus for inserting a prosthesis through an incision into a surgical pocket, comprising: an initial fold abutted to a base fold along the sides opposing the tabs; the initial fold folded over the base fold along the abutted edge; a tab-side seal tuck from the tab to the proximal end; a tab-side seal tuck from the tab to the distal end; a distal end seal tuck from the abutment to the tab-side seal tuck;
   whereby a prosthesis bag is formed with a prosthesis opening and a proximal opening.

5. An apparatus for inserting a prosthesis through an incision into a surgical pocket, comprising: an initial fold abutted to a base fold along the sides opposing the tabs; the initial fold folded over the base fold along the abutted edge; a tab-side seal tuck from the tab to the proximal end; a tab-side seal tuck from the tab to the distal end; a distal end seal tuck from the abutment to the tab-side seal tuck; a distal pocket formed by the distal end seal tuck;
   whereby a prosthesis bag is formed with a prosthesis opening and a proximal opening.

\* \* \* \* \*